US00PP19337P2

(12) United States Plant Patent
Koppe

(10) Patent No.: US PP19,337 P2
(45) Date of Patent: Oct. 14, 2008

(54) *BEGONIA* PLANT NAMED 'GIDEON'

(50) Latin Name: *Begonia×hiemalis*
Varietal Denomination: Gideon

(75) Inventor: Lubbertus H. Koppe, Putten (NL)

(73) Assignee: Koppe Royalty B.V., Ermelo (NL)

( * ) Notice: Subject to any disclaimer, the term of this patent is extended or adjusted under 35 U.S.C. 154(b) by 0 days.

(21) Appl. No.: 11/978,095

(22) Filed: Oct. 25, 2007

(51) Int. Cl.
*A01H 5/00* (2006.01)

(52) U.S. Cl. ..... Plt./348
(58) Field of Classification Search ..... Plt./348
See application file for complete search history.

(56) References Cited

PUBLICATIONS

UPOV–ROM GTITM, Plant Variety Database 2007/06, GTI Jouve Retrieval Software, citation for Begonia 'Gideon'.*

* cited by examiner

*Primary Examiner*—Annette H Para
(74) *Attorney, Agent, or Firm*—C. A. Whealy

(57) ABSTRACT

A new and distinct cultivar of *Begonia* plant named 'Gideon', characterized by its upright and mounded plant habit; freely branching habit; double flowers that are salmon pink in color and held above and beyond the foliage; and excellent postproduction longevity.

1 Drawing Sheet

Botanical designation: *Begonia×hiemalis.*
Cultivar denomination: 'Gideon'.

BACKGROUND OF THE INVENTION

The present invention relates to a new and distinct cultivar of *Begonia* plant, botanically known as *Begonia×hiemalis,* commercially known as Elatior *Begonia* and hereinafter referred to by the name 'Gideon'.

The new *Begonia* is a product of a planned breeding program conducted by the Inventor in Ermelo, The Netherlands. The objective of the breeding program is to create new vigorous *Begonia* cultivars with excellent postproduction longevity.

The new *Begonia* originated from a cross-pollination made by the Inventor in Ermelo, The Netherlands in January, 2001 of an unnamed selection of *Begonia tuberhybrida,* not patented, as the female, or seed, parent with an unnamed selection of *Begonia socotrana,* not patented. The cultivar Elektra Pink was discovered and selected by the Inventor as a flowering plant from within the progeny of the stated cross-pollination in a controlled environment in Ermelo, The Netherlands in June, 2001.

Asexual reproduction of the new *Begonia* by cuttings taken in a controlled environment in Ermelo, the Netherlands since June, 2002, has shown that the unique features of this new *Begonia* are stable and reproduced true to type in successive generations.

SUMMARY OF THE INVENTION

The cultivar Gideon has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Gideon'.

These characteristics in combination distinguish 'Gideon' as a new and distinct *Begonia:*

1. Upright and mounded plant habit.
2. Freely branching habit.
3. Double flowers that are salmon pink in color and held above and beyond the foliage.
4. Excellent postproduction longevity.

Plants of the new *Begonia* differ primarily from plants of the female parent selection in leaf and flower color as plants of the female parent selection have reddish green-colored leaves and light salmon pink-colored flowers.

Plants of the new *Begonia* differ from plants of the male parent selection in the following characteristics:

1. Plants of the new *Begonia* are more freely branching than plants of the male parent selection.
2. Plants of the new *Begonia* have darker green-colored leaves than plants of the male parent selection.
3. Plants of the new *Begonia* have darker pink-colored flowers than plants of the male parent selection.

Plants of the new *Begonia* can also be compared to plants of the cultivar Dark Netja, not patented. In side-by-side comparisons conducted in Ermelo, The Netherlands, plants of the new *Begonia* differed from plants of the cultivar Dark Netja in the following characteristics:

1. Flowers of plants of the new *Begonia* were more double than flowers of plants of the cultivar Dark Netja.
2. Plants of the new *Begonia* and the cultivar Dark Netja differed in flower color as plants of the cultivar Dark Netja had pink and white-colored flowers.

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia.*

The photograph at the top of the sheet comprises a side perspective view of a typical flowering plant of 'Gideon' grown in a container.

The photograph at the bottom of the sheet is a close up view of lower (left) and upper (right) surfaces of typical leaves and flowers of 'Gideon'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Ermelo, The Netherlands, under commercial practice in a glass-covered greenhouse during the spring and summer. Average day and night temperatures were about 20° C. during the first three to four weeks then lowered to an average day and night temperature of 18° C. until flowering. Four weeks after planting rooted cuttings in 12-cm containers, two five-day periods of long nyctoperiods of 16 hours were given and were separated by two days and subsequently followed by short nyctoperiods of eight hours until flowering. Plants were pinched one time about one weeks after planting. Plants were about eleven weeks from planting when the photographs and description were taken.

Botanical classification: *Begonia×hiemalis* cultivar Gideon.
Commercial classification: Elatior *Begonia.*
Parentage:
- *Female, or seed, parent.*—Unnamed selection of *Begonia tuberhybrida,* not patented.
- *Male, or pollen, parent.*—Unnamed selection of *Begonia socotrana,* not patented.

Propagation:
- *Type.*—By terminal vegetative cuttings.
- *Time to develop roots.*—About 20 days at temperatures 20° C.
- *Time to produce a rooted young plant.*—About five weeks at temperatures of 20° C.
- *Root description.*—Fine, fibrous, well-branched; white/orange in color. Plants of the new *Begonia* have not been observed to form tubers.

Plant description:
- *Plant form.*—Compact, upright and mounded plant habit, inverted triangle; freely branching with good stem and stem base strength. Flowers are double and abundant. Plants flower continuously.
- *Growth habit.*—Vigorous growth habit; suitable for 9 to 14-cm containers. Under optimal environmental and cultural conditions, usually about eleven weeks are required to produce proportional 14-cm potted plants from cuttings. Vegetative shoots are formed at basal nodes and flowering shoots are formed at upper nodes.
- *Plant height.*—About 24 cm to 28 cm.
- *Plant width.*—About 35 cm.
- *Leaves.*—Arrangement: Simple, alternate. Developing leaves, length: About 4 cm to 5 cm. Developing leaves, width: About 7 cm to 9 cm. Fully expanded leaves, length: About 10 cm to 11 cm. Fully expanded leaves, width: About 14 cm to 15 cm. Shape: Roughly reniform; oblique. Apex: Obtuse to rounded. Base: Cordate; oblique. Margin: Doubly serrate. Texture, upper surface: Smooth, glabrous; margins, slightly pubescent. Texture, lower surface: Smooth, glabrous. Venation pattern: Palmate. Color: Developing leaves, upper surface: 147A. Developing leaves, lower surface: 148B. Fully expanded leaves, upper surface: Darker than 147A; venation, 146A to 146B. Fully expanded leaves, lower surface: 191A to 191B overlain with 183C; venation, close to 146B. Petiole length: About 2 cm to 9 cm. Petiole texture, upper and lower surfaces: Pubescent. Petiole color, upper and lower surfaces: Close to 146C.

Flower description:
- *Flowering habit.*—Double flowers with numerous tepals arranged in axillary cymes. Usually 15 to 25 flowers per cyme. Many cymes in flower simultaneously. Flowers positioned above and beyond the foliage. Flowering continuous.
- *Natural flowering season.*—Plants will flower year round regardless of nyctoperiod, however plants flower earlier and more abundantly from mid-February until November in the Northern Hemisphere.
- *Flowers.*—Shape: Rounded; rose-like. Diameter: About 5 cm to 6 cm. Depth (height): About 2 cm to 3 cm.
- *Flower buds.*—Length: About 1.2 cm to 2 cm. Diameter: About 1.4 cm to 2.6 cm. Color: Close to 48B.
- *Tepals.*—Arrangement: Rosette. Quantity per flower: Usually about 8 to 22 per flower. Size: Outer tepals, length: About 3 cm to 3.5 cm. Outer tepals, width: About 3.7 cm to 4 cm. Inner tepals, length: About 1.4 cm to 2.5 cm. Inner tepals, width: About 1.6 cm to 2.2 cm. Shape: Rounded flabellate. Apex: Rounded. Margin, outer and inner tepals: Entire. Texture, upper and lower surfaces: Smooth, glabrous; satiny. Color: When opening, upper and lower surfaces: Close to 48B. Fully opened, upper and lower surfaces: Close to 54C.
- *Flower bracts.*—Quantity/arrangement: Two, opposite. Shape: Rounded flabellate. Apex: Acute. Margin: Slightly serrate. Texture, upper and lower surfaces: Smooth, glabrous. Color, upper surface: Close to 146B. Color, lower surface: Close to 144A.
- *Peduncles.*—Angle: Erect. Length: About 6 cm to 7 cm. Texture: Slightly pubescent. Color: Close to 144A.
- *Pedicels.*—Angle: Erect. Length: About 1 cm to 3 cm. Texture: Slightly pubescent. Color: Close to 144A overlain with 170C to 170D.
- *Reproductive organs.*—Stamens: None observed. Pistils: None observed.
- *Seed/fruit.*—Seed and fruit production have not been observed as reproductive organs are not formed.

Postproduction longevity:
- *Individual flowers.*—Generally about two to three weeks.
- *Whole plants.*—About seven weeks under interior conditions.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'Gideon' as illustrated and described.

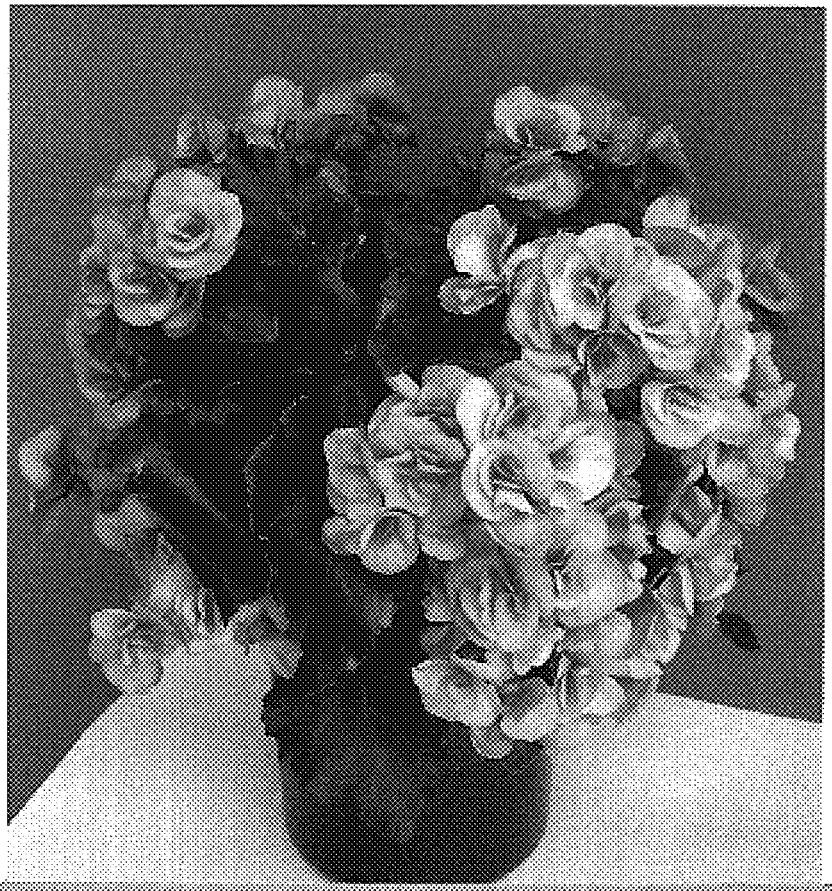
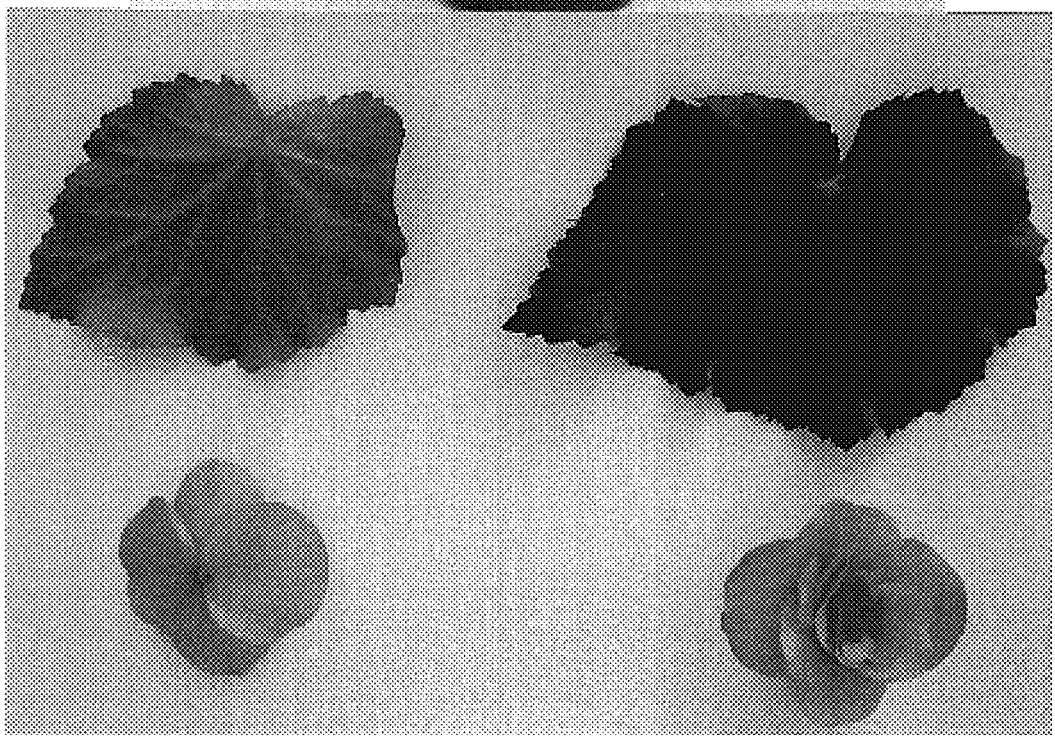

* * * * *